United States Patent
Xia et al.

(10) Patent No.: US 7,244,854 B2
(45) Date of Patent: Jul. 17, 2007

(54) METHOD OF SYNTHESIZING TRIOXYMETHYLENE FROM FORMALDEHYDE BY THE CATALYTIC ACTION OF AN IONIC LIQUID

(75) Inventors: Chungu Xia, Gansu (CN); Zhonghua Tang, Gansu (CN); Jing Chen, Gansu (CN); Xinzhi Zhang, Gansu (CN); Zhen Li, Gansu (CN); Enxiu Guo, Gansu (CN)

(73) Assignee: Lanzhou Institute of Chemical Physics Chinese Academy of Sciences, Lanzhou Gansu (CN)

( * ) Notice: Subject to any disclaimer, the term of this patent is extended or adjusted under 35 U.S.C. 154(b) by 0 days.

(21) Appl. No.: 11/636,156

(22) Filed: Dec. 8, 2006

(65) Prior Publication Data

US 2007/0135649 A1    Jun. 14, 2007

(30) Foreign Application Priority Data

Dec. 9, 2005    (CN) .................. 2005 1 0129885

(51) Int. Cl.
*C07D 323/06* (2006.01)
*C07D 323/04* (2006.01)

(52) U.S. Cl. ...................................... 549/368; 549/367

(58) Field of Classification Search ................. None
See application file for complete search history.

(56) References Cited

U.S. PATENT DOCUMENTS 5,962,702 A * 10/1999 Morishita .................. 549/368

\* cited by examiner

*Primary Examiner*—J. Parsa
(74) *Attorney, Agent, or Firm*—Knobbe, Martens, Olson & Bear, LLP

(57) ABSTRACT

The present invention relates to a method of synthesizing trioxymethylene from formaldehyde by the catalytic action of an acidic ionic liquid. In the method, formaldehyde solution with a concentration of 30~80 wt % is used as reactant, and an ionic liquid is used as catalyst. The cation moiety of the catalyst is selected from either imidazoles cation or pyridines cation, and the anion moiety of the catalyst is selected from one of p-tolyl benzene sulfonate, trifluoromethyl sulfonate, and hydrogen sulfate. In the present invention, ionic liquid is used, for the first time, as a catalyst to synthesize trioxymethylene from formaldehyde. The catalyst can be circularly used for continuous sampling.

4 Claims, No Drawings

METHOD OF SYNTHESIZING TRIOXYMETHYLENE FROM FORMALDEHYDE BY THE CATALYTIC ACTION OF AN IONIC LIQUID

BACKGROUND OF THE INVENTION

1. Field of the Invention

The present invention relates to a method of synthesizing trioxymethylene from formaldehyde by the catalytic action of an acidic ionic liquid.

2. Description of the Related Art

Paraformaldehyde products are widely used in a variety of industries such as car manufacture, machinery, electricity, electronics, instrument, agriculture, manufacture of building materials, light industry, etc., for their superior chemical stability, mechanical strength, and plasticity. Currently, two major methods are used to manufacture paraformaldehyde international-wide, the gaseous formaldehyde method and the trioxymethylene method. Copolymerization technique wherein trioxymethylene is used as polymerizing monomer accounts for 80% paraformaldehyde products all over the world, and therefore techniques for troxymethylene synthesis are essential to paraformaldehyde synthesis. In addition, trioxymethylene is not only useful in the manufacturing of paraformaldehyde resin, but also an important chemical material having a variety of uses such as in the preparation of anhydrous formaldehyde and pesticide, moulding material, bonding material, disinfectant agent, antibacterial agent, etc. Trioxymethylene can be applied to all reactions involving formaldehyde, and is especially useful in reactions employing anhydrous formaldehyde as a reactant.

Currently, sulfuric acid method is commonly used to synthesize trioxymethylene in the industry. However, defects such as high corrosivity of dilute sulfuric acid, high demands on devices used in the method, high cost, large amount of by-products, etc., exist. In 1978, Wells et. al (U.S. Pat. No. 4,110,298) employed polyethylene glycol monobutyl ether as dilutent and used two phase reaction catalyzed by sulfuric acid to produce trioxymethylene. However, the introduction of the third constituent also brought difficulties to the later isolation procedure. Acidic ion exchange resin was used and supported phosphoric acid and sulfuric acid were used as catalysts subsequently (DE-C-1 593 990 and AT-B 252 913, U.S. Pat. No. 5,962,702), however, relatively good result was achieved only with high concentration of formaldehyde and under increased pressure. In 1999, Kashihara et al. (U.S. Pat. No. 5,929,257) reported a constantly stable system of producing trioxymethylene from formalin, in which raw materials need to be pretreated. Yoshida (U.S. Pat. No. 4,381,397, U.S. Pat. No. 4,563,536, Emig (U.S. Pat. No. 5,508,448, U.S. Pat. No. 5,508,449) and Hoffmockel (U.S. Pat. No. 6,124,480) et al. reported respectively in 1983, 1986, 1996, and 2000 that heteropolyacid or supported heteropolyacid was used as catalyst to produce trioxymethylene. However, all these methods need a large amount of catalyst or have high requirement on reaction conditions. In China, GuanJian et al. reported, in 《Natural Gas Chemical Engineering》 (period 5, 2005), that supported PW12/ AC catalyst prepared by dipping active carbon as support in phosphotungstic acid was used to produce trioxymethylene, and the catalyst showed high activity with the relative content of trioxymethylene in gas phase of up to 30%. However, 70% of formaldehyde was used as raw material.

It has been reported that it is cost-effective to use protonic acids (such as sulfuric acid, p-tolyl sulfonic acid etc.) as catalyst to produce trioxymethylene. However, since the protonic acids are highly corrosive, difficult to separate, and cause contamination, zirconium needs to be used as corrosive resistant material on the equipments, which is impractical due to its high cost; when Lewis acid (such as zinc chloride, tantalum pentachloride, bismuth trichloride, titanium tetrachloride, tin tetrachloride etc.) or heteropolyacid or other solid acids are used as catalysts, problems arise such as need for large amount of catalyst, difficult to isolate, and high cost. Therefore, what is needed is a trioxymethylene synthesis system with high-efficiency and low corrosivity, which can achieve effective catalytic circulation, and lower costs of production and investment.

DETAILED DESCRIPTION OF THE PREFERRED EMBODIMENT

It is an object of the present invention to provide a method of producing trioxymethylene from formaldehyde with a catalyst, wherein the reagents used in the method have low corrosivity to the equipment.

The equation of the reaction of the present invention is as follows:

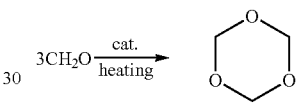

It is another object of the present invention to provide a method of synthesizing trioxymethylene from formaldehyde by the catalysis action of an ionic liquid, wherein the formaldehyde solution with a concentration of 30~80 wt % is used as reactant and an ionic liquid is used as catalyst, and wherein the cation moiety of the catalyst is selected from either imidazoles cation or pyridines cation, and the anion moiety of the catalyst is selected from one of p-tolyl benzene sulfonate, trifluoromethyl sulfonate, and hydrogen sulfate; the content of the catalyst being 0.05~5 wt %.

The formula of the imidazoles cation moiety of the catalyst is:

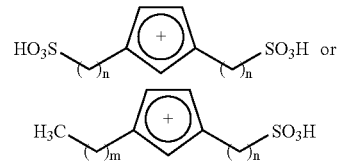

wherein m is an integral of 0-15, and n is an integral of 0-15.

The formula of the pyridines cation moiety of the catalyst is:

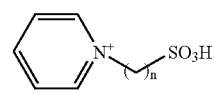

wherein n is an integral of 0-15.

When preparing the catalyst, p-tolyl benzene sulfonic acid, trifluoromethyl sulfonic acid, and sulfonic acid were used to provide anions. The concentration of the acid is 100%, 95% and 98%, respectively.

In the present invention, formaldehyde solution of dealcohol with a concentration of 30~80 wt % was used as reactant.

Continuous sampling rectification device was used in the present invention, with the number of theoretical plates of 7~8, the temperature of the bottom of the rectifying still is 96~98° C., and the temperature of the top of the rectification tower is 92~94° C.

The present invention has the advantages of:

1. Ionic liquid is used, for the first time, as a catalyst to synthesize trioxymethylene from formaldehyde;

2. The catalyst is easy to prepare and has high catalytic activity; the resultants of the reaction contain high concentration of trioxymethylene and less by-products such as methanol, formic acid and methylal etc., which indicates the reaction has superior selectivity;

3. The concentration of the raw formaldehyde can be ranged from 30-80 wt %, and the reaction condition is mild;

4. As a catalyst, less amount (0.05~5 wt %)of ionic liquid is needed in the reaction;

5. The catalyst can be circularly used for continuous sampling;

6. The catalyst has low corrosivity, and therefore does not have special requirement for equipments used;

7. The reaction system generates fewer agglomerations in the reactor, therefore reducing the needs to clean the reactor.

EXAMPLES

The rectification reaction device used in the present invention has a rectification section with an inner diameter of 30 mm, and a glass filled tower loaded with filling materials of type θ2.0 mm×2.0 mm 316 L stainless steel rasching with a filling height of 0.3 m. The number of plates is 7~8. The reactor used is a three necked bottle of 250 ml. The condenser on the top of the rectification section is an electromagnetism relay type condenses head. Reflux ratio is set, controlled and modulated by time programmed controller.

The structure of the catalyst are as follows:

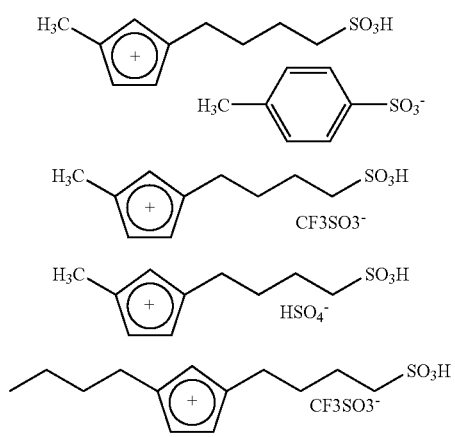

-continued

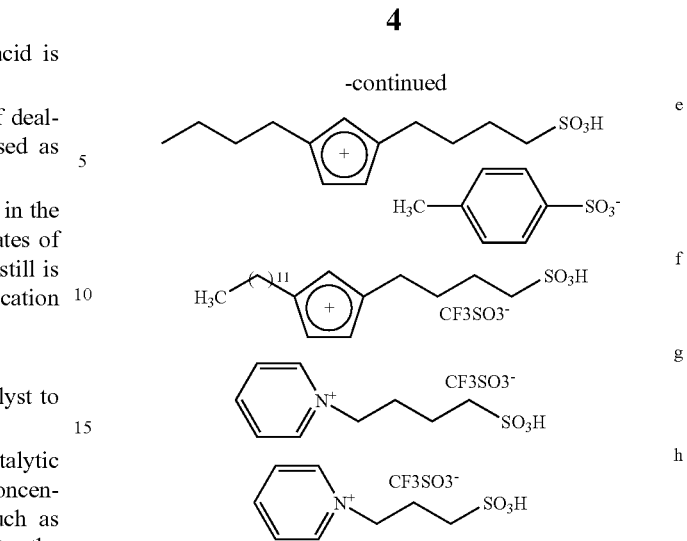

EXAMPLE 1

100 g of 50.1% formaldehyde solution (containing 1.7% of methanol) and 2.6 g of catalyst a were added sequentially into a 250ml reactor. The reactants were heated and refluxed sufficiently for 2 h. Then, the reflux ratio was adjusted to R=2 to evaporate formaldehyde, trioxymethylene, and water azeotropic mixture off from the top of the reactor. At the same time, 50 g of 50.1% formaldehyde solution was added into the reactor with a feeding speed of 0.8 ml/min. The temperature of the bottom of the rectifying still is 96.5° C., and the temperature of the top of the tower is 92° C. After 3 hs' reaction, chromatographic analysis result indicates the resultant distillate contains 21.5% of trioxymethylene, 2.1% of methanol, and 1.3% of methylal.

EXAMPLE 2

The same as in example 1, except 1.0 g of catalyst b was added into 110 g of 51.2% formaldehyde solution (containing 1.5% of methanol). The temperature of the bottom of the rectifying still is 96-97° C., and the temperature of the top of the tower is 94° C. Chromatographic analysis result indicates the resultant distillate contains 24.9% of trioxymethylene, 2.0% of methanol, and 0.8% of methylal.

EXAMPLE 3

The same as in example 1, except 3.0 g of catalyst c was added into 100 g of 50.3% formaldehyde solution (containing 1.7% of methanol). The temperature of the bottom of the rectifying still is 96° C., and the temperature of the top of the tower is 94° C. Chromatographic analysis result indicates the resultant distillate contains 17.8% of trioxymethylene, 2.5% of methanol, and 1.6% of methylal.

EXAMPLE 4

The same as in example 1, except 1.5 g of catalyst d was added into 100 g of 50.3% formaldehyde solution (containing 1.7% of methanol). The temperature of the bottom of the rectifying still is 96.5° C., and the temperature of the top of the tower is 93.5-94° C. Chromatographic analysis result indicates the resultant distillate contains 22.7% of trioxymethylene, 2.2% of methanol, and 2.4% of methylal.

EXAMPLE 5

The same as in example 1, except 2.8 g of catalyst e was added into 110 g of 51.2% formaldehyde solution (containing 1.5% of methanol). The temperature of the bottom of the rectifying still is 96.5-98° C., and the temperature of the top of the tower is 92-93° C. Chromatographic analysis result indicates the resultant distillate contains 18.2% of trioxymethylene, 2.0% of methanol, and 1.6% of methylal.

EXAMPLE 6

The same as in example 1, except 1.5 g of catalyst f was added into 100 g of 50.2% formaldehyde solution (containing 1.7% of methanol). The temperature of the bottom of the rectifying still is 96-96.5° C., and the temperature of the top of the tower is 92-93° C. Chromatographic analysis result indicates the resultant distillate contains 20.1% of trioxymethylene, 2.4% of methanol, and 1.9% of methylal.

EXAMPLE 7

The same as in example 1, except 1.2 g of catalyst g was added into 100 g of 51.4% formaldehyde solution (containing 1.5% of methanol). The temperature of the bottom of the rectifying still is 96-97° C., and the temperature of the top of the tower is 92-92.5° C. Chromatographic analysis result indicates the resultant distillate contains 22.4% of trioxymethylene, 2.3% of methanol, and 2.1% of methylal.

EXAMPLE 8

The same as in example 1, except 1.2 g of catalyst h was added into 100 g of 50.3% formaldehyde solution (containing 1.7% of methanol). The temperature of the bottom of the rectifying still is 96.5-97° C., and the temperature of the top of the tower is 93-94° C. Chromatographic analysis result indicates the resultant distillate contains 18.5% of trioxymethylene, 2.1% of methanol, and 2.6% of methylal.

EXAMPLE 9

The same as in example 1, except 1.1 g of catalyst b was weighted and added into 100 g of 54.6% formaldehyde solution (containing 1.3% of methanol). The temperature of the bottom of the rectifying still is 96-97° C., and the temperature of the top of the tower is 94° C. After 1h's reaction, chromatographic analysis result indicates the resultant distillate contains 23.7% of trioxymethylene. The temperature was reduced by switching off the power for 48 hs, and polymers (white solid) appeared in the bottom of the reactor. When temperature was increased to 80° C., the solution in the bottom became clear again. Samples were taken when the temperature of the reactor bottom reached 96° C., and chromatographic analysis result indicates the resultant distillate contains 22.7% of trioxymethylene, 2.2% of methanol, and 1.4% of methylal.

EXAMPLE 10

The same as in example 1, except 1.3 g of catalyst b was weighted and added into 130 g of 52.1% formaldehyde solution (containing 1.3% of methanol). The temperature of the bottom of the rectifying still is 96-97° C., and the temperature of the top of the tower is 94° C. After 4 hs' reaction, chromatographic analysis result indicates the resultant distillate contains 30.2% of trioxymethylene, 1.8% of methanol, and 0.8% of methylal. The content of the formic acid measured by acid-base titration is 334 ppm.

EXAMPLE 11

The same as in example 1, except 1.0 g of catalyst b was weighted and added into 100 g of 41.6% formaldehyde solution (containing 1.8% of methanol). The temperature of the bottom of the rectifying still is 96.5° C., and the temperature of the top of the tower is 94° C. After 4 hs' reaction, chromatographic analysis result indicates the resultant distillate contains 31.0% of trioxymethylene, 2.3% of methanol, and 1.2% of methylal. The content of the formic acid measured by acid-base titration is 301 ppm.

What is claimed is:

1. A method of synthesizing trioxymethylene from formaldehyde solution by the catalytic action of an ionic liquid, comprising reacting the formaldehyde solution with a concentration of 30~80 wt % as reactant with an ionic liquid as catalyst, wherein the cation moiety of the catalyst is selected from imidazoles cation or pyridines cation; the anion moiety of the catalyst is selected from one of p-tolyl benzene sulfonate, trifluoromethyl sulfonate, and hydrogen sulfate; and the content of the catalyst is 0.05~5 wt %.

2. The method of claim 1, wherein the formula of the cation catalyst of imidazoles is

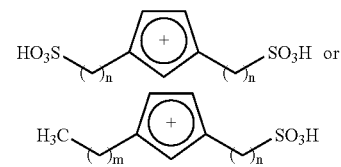

wherein m is an integral of 0-15, and n is an integral of 0-15.

3. The method of claim 1, wherein the formula of the cation catalyst of pyridines is

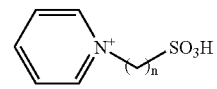

wherein n is an integral of 0-15.

4. The method of claim 1, wherein continuous sampling rectification device is used in the reaction with the number of theoretical plates of 7~8, the temperature of the bottom of rectifying still is 96~98° C., and the temperature of the top of the rectification tower is 92~94° C.

* * * * *